United States Patent [19]
Tanaka et al.

[11] Patent Number: 5,588,745
[45] Date of Patent: Dec. 31, 1996

[54] METHODS AND APPARATUS FOR MIXING BONE CEMENT COMPONENTS USING AN EVACUATED MIXING CHAMBER

[75] Inventors: Kazuna Tanaka, Cos Cob; Jeffrey Kapec, Westport, both of Conn.; Allan B. Chochinov, New York, N.Y.

[73] Assignee: Howmedica

[21] Appl. No.: 300,045

[22] Filed: Sep. 2, 1994

[51] Int. Cl.⁶ .............................. B01F 13/06; B01F 15/02
[52] U.S. Cl. ...................... 366/130; 366/139; 366/163.1; 366/178.2; 206/222
[58] Field of Search ...................................... 366/129, 130, 366/139, 178.1, 163.1, 167.1, 169.1, 169.2, 182.1, 184, 189, 194–196, 308, 178.2; 206/219, 222; 604/410, 411, 413–416, 903; 606/86, 92–94

[56] References Cited

U.S. PATENT DOCUMENTS

| | | |
|---|---|---|
| 3,700,215 | 10/1972 | Hardman et al. . |
| 4,463,875 | 8/1984 | Tepic ..................... 206/219 X |
| 4,758,096 | 7/1988 | Gunnarsson . |
| 4,966,601 | 10/1990 | Draenert . |
| 4,973,168 | 11/1990 | Chan . |
| 5,051,482 | 9/1991 | Tepic . |
| 5,100,241 | 3/1992 | Chan . |
| 5,114,240 | 5/1992 | Kindt-Larsen et al. . |
| 5,193,907 | 3/1993 | Faccioli et al. ...................... 366/139 X |
| 5,236,418 | 8/1993 | Kriesel . |
| 5,370,221 | 12/1994 | Magnusson et al. ............... 604/416 X |
| 5,398,483 | 3/1995 | Smith et al. ......................... 206/219 X |
| 5,435,645 | 7/1995 | Faccioli et al. ..................... 366/139 X |

FOREIGN PATENT DOCUMENTS

| | | |
|---|---|---|
| 402669 | 12/1990 | European Pat. Off. . |
| 2921565 | 12/1980 | Germany .................................. 606/93 |
| 3814377 | 11/1989 | Germany . |

*Primary Examiner*—Charles E. Cooley
*Attorney, Agent, or Firm*—Joseph J. Kaliko

[57] ABSTRACT

Methods and apparatus are set forth for preparing and delivering bone cement formed by combining a powdered polymer component and a liquid monomer component. The powdered polymer component is stored in an evacuated mixing chamber. The liquid monomer component, according to one specific aspect of the invention, is introduced into the mixing chamber by a control mechanism which causes the stored powder to be "substantially wet", i.e., all of the powdered polymer component is wet to at least some degree and is otherwise devoid of powder pockets. The control mechanism, according to a preferred embodiment of the invention, stages the release of the liquid monomer into the vacuum packed powder chamber, under the effect of the vacuum, in a timed sequence using a plurality of monomer distribution channels. The distribution channels, which in a preferred embodiment of the invention include liquid component diffusers, insure the substantial wetting of the stored powder by delivering the liquid in parallel to different portions of the mixing chamber. The substantial wetting of the powder is designed to ultimately insure a homogeneous bone cement mix.

73 Claims, 3 Drawing Sheets

METHODS AND APPARATUS FOR MIXING BONE CEMENT COMPONENTS USING AN EVACUATED MIXING CHAMBER

BACKGROUND OF THE INVENTION

1. Field of the Invention

The invention relates generally to methods and apparatus for preparing and delivering a self curing bone cement formed as a polymeric reaction product after mixing a powdered polymer component with a liquid monomer component.

More particularly, the invention relates to methods and apparatus for preparing and delivering bone cement by combining a powdered polymer component stored in an evacuated mixing chamber with a liquid monomer component stored in a pressurized chamber (e.g., under atmospheric pressure), where the vacuum is used to draw the liquid into the mixing chamber at a desired point in time.

According to one specific aspect of the invention, the liquid monomer is introduced into the evacuated mixing chamber by control means which causes the stored powder to be "substantially wet". As used herein the term "substantially wet" is defined to mean all of the powdered polymer component is wet to at least some degree and is otherwise devoid of powder pockets.

The control means, according to a preferred embodiment of the invention, stages the release of the liquid monomer into the vacuum packed powder chamber, under the effect of the vacuum, in a timed sequence using a plurality of monomer distribution channels.

The distribution channels, which include liquid component diffusion means, insure the substantial wetting of the stored powder by delivering the liquid in parallel to different portions of the evacuated mixing chamber. The substantial wetting of the powder is designed to ultimately insure a homogeneous bone cement mix.

2. Brief Description of the Prior Art

In many orthopedic surgical procedures it is necessary to employ a bonding material to set implants such as pins and artificial joints in bone. The demand for bone cement for such applications has increased in spite of the growth of cementless implant technology. This is because bone cement has distinct indications and a surgeon will usually specify a cement based upon its tensile strength and workability.

The cement employed for surgical purposes is generally a polymeric material which is prepared by copolymerization of its components as needed. Because of the necessity for a fairly quick setting material the cement is almost universally prepared by a surgical assistant during the course of the operation in the sterile field of the operating room. The preparation of the cement involves mixing the aforementioned components in a suitable vessel.

The cement is usually a (meth)acrylic material which is a reaction product of a monomer and a polymer, e.g., methylmethacrylate monomer and polymethylmethacrylate or methylmethacrylate-styrene copolymer. In order to provide a cement which has the desired properties and which has the desired fixation of the implants, it is necessary that the compounds be uniformly and thoroughly mixed so that a homogeneous reaction product is produced.

Many systems exist for the preparation and delivery of a polymethylmetacrylate bone cement formed from powdered polymer and liquid monomer components. However, the known systems have various shortcomings, to be discussed hereinafter, which make a quality cement (in terms of strength, durability, etc.), difficult to prepare.

Careful mixing is required to maximize the amount of powder that is wet and to keep out (and/or remove) as much air as possible from the mixture. Failure to achieve these two objectives can result in unpolymerized powder contaminating and/or air bubbles weakening the final reaction product cement mixture. These contaminants have the potential for compromising the long term performance of the cement and any associated implant.

Furthermore, the known processes for mixing polymethylmetacrylate cement are often complicated by the need to deal with noxious fumes produced when the aforementioned components are mixed, and because the useful working time for the cement (time before it hardens) is short.

In spite of the aforementioned difficulties, manufacturers have made conscientious efforts to improve systems for preparing and delivering bone cement by, for example, using component mixing chambers connected to vacuum pumps to filter fumes; providing mixing paddles to try and produce a more uniform cement mixture; using compression techniques to "squeeze" out air from the mixture; using dispensing guns to eject premixed material loaded into the gun, and so on.

These known systems are inherently problematic from several reasons. Vacuum tubes must be hooked up; mixing paddles must be engaged and do not insure uniform saturation of the powder component; the noxious fumes must be drawn away from the mixing site; and any premixed cement must actually be placed into the dispensing apparatus.

Furthermore, the two components themselves must be removed from separate packaging and be placed into a mixing chamber. The separate packaging is required since the monomer and cement powder can not be sterilized in the same manner. The liquid component requires aseptic packaging, while the powder component must be gamma sterilized.

The two sterile packages are typically comprised of different structures (usually a glass vial for the liquid and a plastic packet for the powder). Furthermore, the two components have different consistencies, densities and mixing properties. All of the aforementioned factors make the critical mixing sequence difficult.

The prior art has attempted to address many of the aforementioned problems by, for example, utilizing compressive force to remove air from a cement mixture as the cement is being formed; by using a vacuum packed solid component chamber to draw the liquid component into spaces between the solid particles in an attempt to achieve a more uniform component mixture; by filtering fumes created during the reaction process, as will be explained hereinafter with reference to several issued patents which exemplify the state of the art.

In particular, Gunnarsson, in U.S. Pat. No. 4,758,096; Draenert, in U.S. Pat. No. 4,996,601; Tepic, in U.S. Pat. No. 5,051,482; Chan, in U.S. Pat. Nos. 4,973,168 and 5,100,241; and Kindt-Larsen et al., in U.S. Pat. No. 5,114,240 (and corresponding Danish Patent Number 2355/89), are referred to hereinafter to illustrate the present state of the bone cement preparation and delivery art.

These patents are broadly directed to two types of systems. Systems that use a vacuum for the mixing process and systems that use a compressive force to mix the bone cement components.

In particular, Gunnarsson, in U.S. Pat. No. 4,758,096, issued Jul. 19, 1988, is a background reference which teaches apparatus for mixing bone cement components in a vacuum. The reference cites minimizing the potential for air remaining in the reaction product as the principal advantage of mixing the cement in an evacuated container.

The Gunnarsson reference requires that the mixing container be connected to an external vacuum source after the components of the bone cement are first placed into the mixing container. Once under a vacuum, the components are manually agitated to create the mix.

Such a system, although reducing the amount of air in the mixture by performing the mixing process in a vacuum, does little to insure that all of the powder is wet before the reaction process begins. As indicated hereinabove, failure to address this problem can result in inclusions being formed in the finished cement product as a result of unpolymerized powder being included in the mix.

Furthermore, the teachings of Gunnarsson require the use of a separate vacuum pump to evacuate the mixing chamber (once the components are placed therein), with the vacuum pump requiring manual hookup and a start up delay before the mixing process can begin. This delay takes valuable time away from being able to achieve a thorough mix since the reactive components have already been placed together (and are reacting to one another) in the mixing chamber.

Further examples of techniques for mixing bone cement components in a vacuum are described by Tepic, in U.S. Pat. No. 5,051,482; and Chan, in U.S. Pat. No. 4,973,168 and 5,100,241.

Tepic, in U.S. Pat. No. 5,051,482, issued Sep. 24, 1991, describes methods and apparatus for preparing a self-curing two-component powder liquid bone cement using a vacuum packed powder chamber into which monomer is introduced. The Tepic system was designed to eliminate the need for mechanical stirring as, for example, required by Gunnarsson.

Nevertheless, Tepic, like Gunnarsson, did not solve or even address the problem of insuring that all of the powder is thoroughly saturated with the liquid bone cement component before the reaction process begins.

In particular, utilizing the teachings of Tepic, the powder polymer can not be sufficiently infused with liquid monomer so as to produce a proper cement mixture. The initial portion of monomer introduced into the powder starts to catalyze with the powder thereby creating a blockage for the remaining monomer.

As a result, the balance of the monomer can not find its way past such an obstruction, or "clog", thereby depriving the rest of the powder of any monomer whatsoever causing substantial amounts of powder to remained dry and unmixed. Similar shortcomings are inherent in all known vacuum mix systems, including the Chan patents discussed hereinafter.

Chan, in U.S. Pat. No. 5,100,241, issued Mar. 31, 1992, and U.S. Pat. No. 4,973,168, teaches a two-component bone cement mixing system comprising a cartridge mixer having an interior volume containing a first predetermined quantity of a free-flowing, powdery, solid bone cement component under vacuum pressure, an ampoule containing a second predetermined quantity of a liquid bone cement component, and a fluid transfer mechanism for fluidically connecting the cartridge mixer and ampoule.

The two-component bone cement mixing system described by Chan allows in vacuo mixing of liquid monomeric and solid polymeric bone cement components without air being incorporated into the mixture and prevents the passage of air into the cartridge mixer during and/or after monomeric transfer. The mixing process itself is carried out by causing reciprocating motion of a mixing element within the cartridge mixer.

Chan however, like the other references cited hereinabove, fails to teach, claim or even suggest methods and apparatus which insure that all of the powder is thoroughly saturated with the liquid bone cement component before the reaction process begins.

Furthermore, Chan's system for admixing bone cement components under vacuum pressure contemplates using a predetermined degree of chilling to control the rate of hardening of the cement, and subsequent pressurizing of the admixture to help inhibit entrainment of gaseous materials in the cement mix.

Accordingly, the system contemplated by Chan not only fails to solve the problem of substantially (thoroughly) wetting the powder, but is unduly complicated to operate.

Draenert, in U.S. Pat. No. 4,996,601, issued Oct. 30, 1990, describes apparatus for mixing and applying bone cement using an evacuatable bone cement syringe. The syringe system described includes a container for receiving the bone cement prior to its application, a pressure generating apparatus for precompressing the bone cement in the container; and a bell, comprising a vacuum tube, placed over the container (and held by a flange) so that the gases which escape during the process of decompression can be sucked off to reduce the porosity of the bone cement being applied.

It should be noted that the vacuum used in the Draenert system is for outgassing purposes (not for mixing the bone cement components as described by the other references cited hereinbefore), and that Draenert uses compressive force to squeeze air out from the cement mixture. Furthermore, Draenert completely fails to teach, claim or even suggest how to solve the aforementioned uniform mixing (thorough powder saturation) problem recited hereinbefore.

Finally, the present state of the art can be more fully appreciated with reference to an alternate approach to using a vacuum to mix bone cement described by Kindt-Larsen et al., in U.S. Pat. No. 5,114,240, issued May 19, 1992 (also described in corresponding Danish Patent Number 2355/89); and with further reference to copending patent application Ser. No. 08/076,556, entitled "Methods and Apparatus For Preparing and Delivering Bone Cement", filed Jun. 11, 1993 and assigned to the same assignee as the present invention. The copending patent application is hereby incorporated by reference.

According to Kindt-Larsen et al., a paste like material is provided by a mixing device that includes a first cylinder for containing a powdered component and a second cylinder for containing a liquid component. The first cylinder has a closed first end and an opposite second end provided with venting means. The second cylinder has a closed first end and an opposite second end sealingly receiving the closed first end of the first cylinder together in a piston-like manner.

The device also includes means for communicating between the inner spaces of the first and second cylinders through the closed first end of the first cylinder, whereby liquid from the second cylinder is injected into interstices defined between the powdered component contained in the first cylinder for providing a paste-like cementitious material when the first cylinder is forced into the second cylinder.

The Kinde-Larsen et al. device operates by using pressure developed by a caulking gun to force the isolated powder and liquid components together. In particular, liquid monomer is forced through the stored powder removing air from the powder compartment. The air and gasses developed during the polymerization process are vented through an activated carbon filter. Both the air and fumes are expelled by compressing the two components together.

As indicated hereinbefore, systems like the one disclosed in the Kindt-Larsen et al. reference are prone to produce cement having inclusions caused by entrapped air bubbles not removed by the applied compressive force and inclusions caused by unpolymerized powder. Furthermore, the type of system described by Kindt-Larsen et al., requires fumes be expelled and filtered while the mixing process takes place; requiring a charcoal filter to absorb the fumes and requiring the use of a relatively unreliable force (a manually applied compressive force), to mix the monomer and powder, and to squeeze out gasses.

The incorporated patent application relates to methods and apparatus for preparing and delivering bone cement by simultaneously injecting powder and liquid components (previously sterilized and stored in separate component chambers), into an evacuated mixing chamber; uniformly mixing the components therein (to substantially wet the powder); and delivering the cement formed by the polymerization process, as needed in an operative setting, utilizing a single ready to use device.

The uniform mix is achieved by simultaneously subjecting the contents of the component chambers to the effects of the mixing chamber's vacuum via separate one way nozzles, interconnecting the component chambers to the mixing chamber, which cause the powder to be broadcast and liquid to be sprayed into the mixing chamber. The nozzles are designed and oriented in a predetermined manner (depending on the type and quantity of the constituent bone cement components being mixed), to cause the components to interact at a preselected distance within the mixing chamber, to assure uniform powder saturation and a thorough mix which yields a homogeneous reaction product.

Although producing a high quality cement mix, the "injection" technique taught in the incorporated copending patent application is a three chambered device (two storage chambers and one mixing chamber), and requires the use of the aforementioned specially designed nozzles to cause the components to interact at a preselected distance within the mixing chamber.

In view of the state of the art as illustrated by the aforementioned references, it would be desirable to provide methods and apparatus which reduce the potential for unpolymerized powder contaminating the cement mixture formed as a reaction product to the aforementioned powdered and liquid bone cement components.

To this end it would be desirable to provide methods and apparatus which produce a uniform powder/monomer mix, with the monomer wetting as much powder as possible before polymerization begins to thereby improve cement durability.

It would be further desirable to provide methods and apparatus which not only substantially wet the powder with the liquid monomer component, but which also keep, as well as remove, as much air as possible out of the resulting reaction product cement mixture to minimize the potential for air bubble inclusions in the reaction product to further increase cement durability.

Still further, it would be desirable to provide methods and apparatus which do not require the use of vacuum pumps, vacuum hoses, separate venting systems, filters, etc., to deal with the venting of noxious fumes and other gases produced when the aforementioned components are mixed.

Further yet, it would be desirable to provide methods and apparatus which enable bone cement to be prepared using a single ready to use two chamber device not requiring the addition of bone cement components, vacuum hookups, etc., which maintains the integrity of the sterile bone cement components throughout the cement preparation operation and which is designed to cooperate with a cement delivery unit to complete the cement preparation and delivery process.

It would also be desirable to provide methods and apparatus for preparing bone cement which do not require that the reactive components be brought together prior to performing the mixing operation per se; which utilize the effects of a vacuum to introduce the liquid component into an evacuated packed powder chamber in a manner designed to insure that the powder is substantially wet; and which uniformly mixes the powdered component and liquid component within the mixing chamber to thereby saturate the powdered component with the liquid component.

SUMMARY OF THE INVENTION

Accordingly, it is an object of the invention to provide methods and apparatus which reduce the potential for unpolymerized powder contaminating the cement mixture formed as a reaction product to the aforementioned powdered and liquid bone cement components.

In furtherance of this objective, it is another object of the invention to provide methods and apparatus which produce a uniform powder/monomer mix having as much powder as possible saturated by the liquid monomer before polymerization begins.

A further object of the invention is to provide methods and apparatus which not only thoroughly wets the powder with the liquid monomer component, but which also keep, as well as remove, as much air as possible out of the resulting reaction product cement mixture.

Still further, it is an object of the invention to provide methods and apparatus which do not require the use of vacuum pumps, vacuum hoses, separate venting systems, filters, etc., to venting noxious fumes and other gases produced when the aforementioned components are mixed.

Further yet, it is an object of the invention to provide methods and apparatus which enable bone cement to be prepared using a single ready to use two chamber cement preparation device not requiring the addition of bone cement components, vacuum hookups, etc., and which maintains the integrity of the sterile bone cement components throughout the cement preparation operation.

Yet another object of the invention is to provide a cement delivery capability by utilizing a standard, commercially available caulking gun in cooperation with the aforementioned single ready to use cement preparation device, to complete the cement preparation and delivery process.

Still further objects of the invention are to provide methods and apparatus for preparing and delivering bone cement which do not require that the reactive components be brought together prior to performing the mixing operation per se; which utilize the effects of a vacuum to introduce the liquid component into an evacuated packed powder chamber in a manner designed to insure that the powder is substantially wet; and which uniformly mixes the powdered component and liquid component within the mixing chamber to thereby saturate the powdered component with the liquid component.

According to a first aspect of the invention, a liquid monomer bone cement component is introduced into an evacuated mixing chamber containing a powdered polymer bone cement component by control means which causes the stored powder to be "substantially wet" as defined hereinbefore, i.e., all of the powdered polymer component is wet to at least some degree and is otherwise devoid of powder pockets.

The control means, according to a preferred embodiment of the invention, stages the release of the liquid monomer into the vacuum packed powder chamber, under the effect of the vacuum, in a timed sequence using a plurality of monomer distribution channels.

The distribution channels, which include liquid component diffusion means, insure the substantial wetting of the stored powder by delivering the liquid in parallel to different portions of the evacuated mixing chamber. The substantial wetting of the powder is designed to ultimately insure a homogeneous bone cement mix.

According to one specific aspect of the invention, apparatus for preparing a homogeneous self-curing two component powder/liquid bone cement using a vacuum packed powdered polymer chamber into which liquid monomer is introduced, comprises: (a) a pressurized chamber for storing the liquid monomer; (b) a vacuum packed powder chamber for storing the powdered polymer; and (c) means for controlling the introduction of the liquid monomer into the vacuum packed powder chamber to substantially wet the powdered polymer stored therein.

An alternate embodiment of the invention, which is directed to insuring a thoroughly mix of the bone cement components once brought together (i.e., after the powder is wet), may be characterized as apparatus for preparing and delivering a self curing bone cement formed as a polymeric reaction product when a powdered polymer component is mixed with a liquid monomer component, comprising: (a) an evacuated first component chamber for storing a powdered polymer component; (b) a second component chamber for storing a liquid monomer component; (c) means for controlling the introduction of the liquid monomer component stored the second component chamber to a multiplicity of different locations within the first component chamber to substantially wet the powdered polymer component stored therein; and (d) means for uniformly mixing the powdered polymer component and the liquid monomer component within the first component chamber thereby saturating the powdered polymer component with the liquid monomer component.

Yet another embodiment of the invention, not limited to bone cement preparation per se, contemplates a mixing device for mixing a powdered and a liquid component.

One such mixing device comprises: (a) a first evacuated container containing a powdered component; (b) a second container containing a liquid component; (c) means for connecting the first and second containers, after the evacuation of the first container, allowing liquid component to be drawn into the first container; and (d) means for introducing the liquid component into the first chamber in a manner which substantially wets the powdered component stored therein.

The invention also contemplates methods for preparing bone cement from a liquid monomer component and a powdered polymer component; methods for mixing powdered and liquid components in general; and methods for saturating a powdered component with a liquid component, all designed to insure that the powder is substantially wet when the component are brought together using vacuum force. These processes all enhance the prospect of obtaining a homogeneous component mixture whether preparing a bone cement mix or some other component mixture in an application not related to bone cement preparation.

A specific example of one such method is a method for preparing and delivering self curing bone cement formed by combining a powdered polymer component and a liquid monomer component, comprising the steps of: (a) storing the powdered polymer component in an evacuated mixing chamber; (b) storing the liquid monomer component in a separate pressurized component chamber; and (c) controlling the introduction of the liquid monomer component into the mixing chamber to substantially wet the powdered polymer component stored therein.

Yet another aspect of the invention is directed to a novel plunger head per se, for use as part of a system for mixing a powdered component, stored in an evacuated mixing chamber into which the distal end of the plunger head extends, with a liquid component, stored in a pressurized chamber attached to the proximate end of the plunger head.

As a specific example, a plunger head contemplated by one aspect of the invention comprises: (a) means for controlling the introduction of a liquid component, stored in a pressurized chamber, to a multiplicity of different locations within an evacuated mixing chamber to substantially wet a powdered component stored therein, combined with (b) means for uniformly mixing the powdered component and the liquid component within the mixing chamber to thereby saturate the powdered component with the liquid component.

The invention is also directed to products of the processes employing the teachings of the invention.

The invention features methods and apparatus for preparing bone cement, and other mixtures of powdered and liquid components that need to be uniformly mixed, utilizing a single ready to use two chamber device that includes an evacuated packed powder component chamber and a separate pressurized liquid component chamber. The vacuum in the powder component chamber, along with control means contemplated by the invention, is used to distribute the liquid component throughout the powder chamber in a uniform and controlled manner to ensure a homogeneous mix of the components. In the bone cement application, the homogeneous mix increases the durability of the cement. No separate attachment of vacuum hoses or separate venting system for air and/or fumes are needed to practice the invention.

These and other objects, embodiments and features of the present invention and the manner of obtaining them will become apparent to those skilled in the art, and the invention itself will be best understood by reference to the following Detailed Description read in conjunction with the accompanying Drawing.

DETAILED DESCRIPTION

Figure 1:
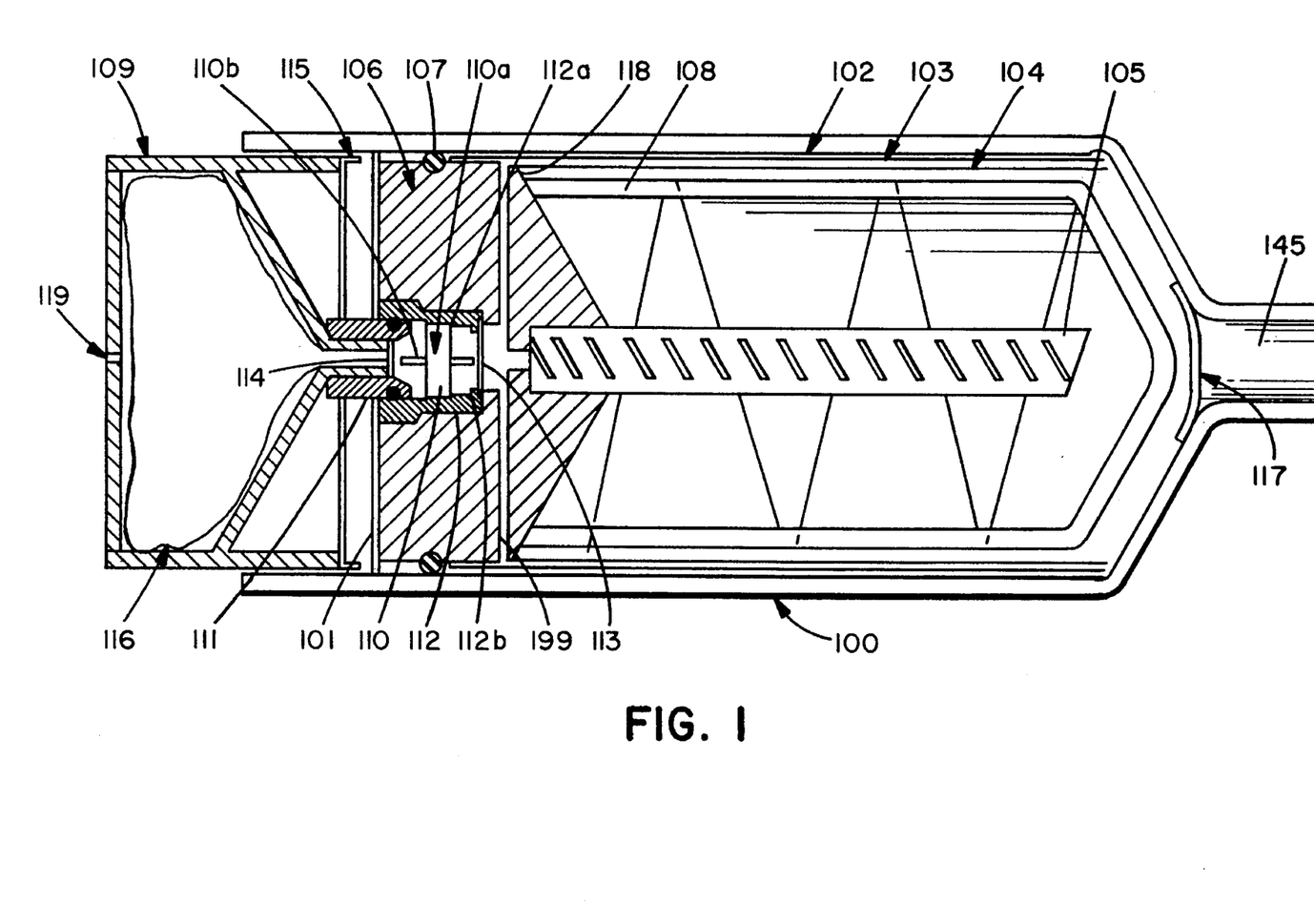
FIG. 1 is a partial elevational sectional view of an illustrative bone cement preparation and delivery device contemplated by the invention. The device is shown in a ready for use state.

An illustrative bone cement preparation and delivery device which incorporates the teachings of a preferred embodiment the invention, and which may be used to illustrate various aspects of the invention which were described hereinabove, is depicted in FIG. 1. The device shown in FIG. 1 is depicted in a ready for use state.

In particular, FIG. 1 shows a set of components that in the depicted combination (forming device 100) work together in a timed sequence, staging the release of the monomer into a vacuum/powder/mixing chamber to be more fully described hereinafter with specific reference to the Drawing. The monomer is distributed throughout the powder chamber in a uniform and controlled manner to ensure a homogeneous mix of the bone cement.

Figure 2:
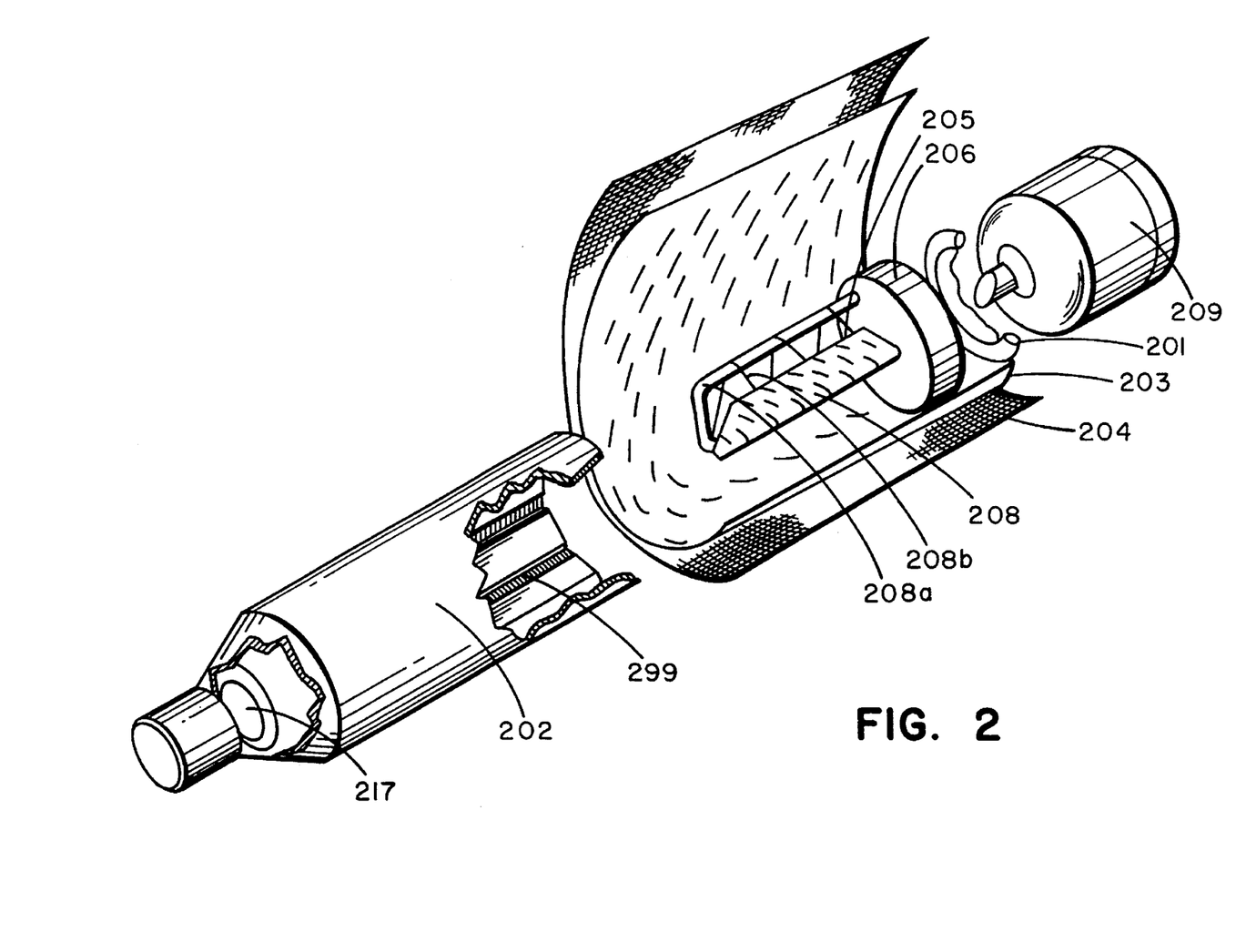
FIG. 2 is depicts an exemplary stirring rod assembly of the type shown attached to the plunger head in FIG. 1, along with exemplary liquid component diffusion means which are both, according to a preferred embodiment of the invention, installed in the vacuum, packed powder chamber depicted in FIG. 1.

The components depicted in the illustrative embodiment of the invention shown in FIG. 1 are: primary vacuum seal 101; powder/vacuum chamber 102 (also sometimes referred to herein as the "mixing" chamber); wire mesh screen 103; monomer circumferential diffuser with slitted plastic tube 104; monomer core diffuser with slitted plastic tube 105; plunger head 106; plunger seal 107; stirring rod assembly 108 (including rod 208a and collapsing wire filament 208b shown in FIG. 2); monomer chamber 109; hollow needle knife blade assembly 110, including knife blade collar 110a and knife blade tube 110b (note double edge knife blade configuration for piercing proximal and distal membrane seals); inner membrane mounting blocks 111 for membrane seal facing monomer chamber 109 (identified hereinafter as membrane seal 114); knife blade collar with timing step 112; timing step ridge 112a projecting into the lumen of knife blade assembly 110; knife blade assembly retainer ridge 112b; membrane seal 113 facing powder/vacuum chamber 102; membrane seal 114 facing monomer chamber 109; knife blade 115 used to pierce primary vacuum seal (e.g. a micro serrated blade); flexible bladder 116 (shown in monomer chamber 109); distal vacuum chamber seal 117; scraper blade 118 (to remove all mixture from chamber walls); and monomer chamber vent 119.

Figure 1A:
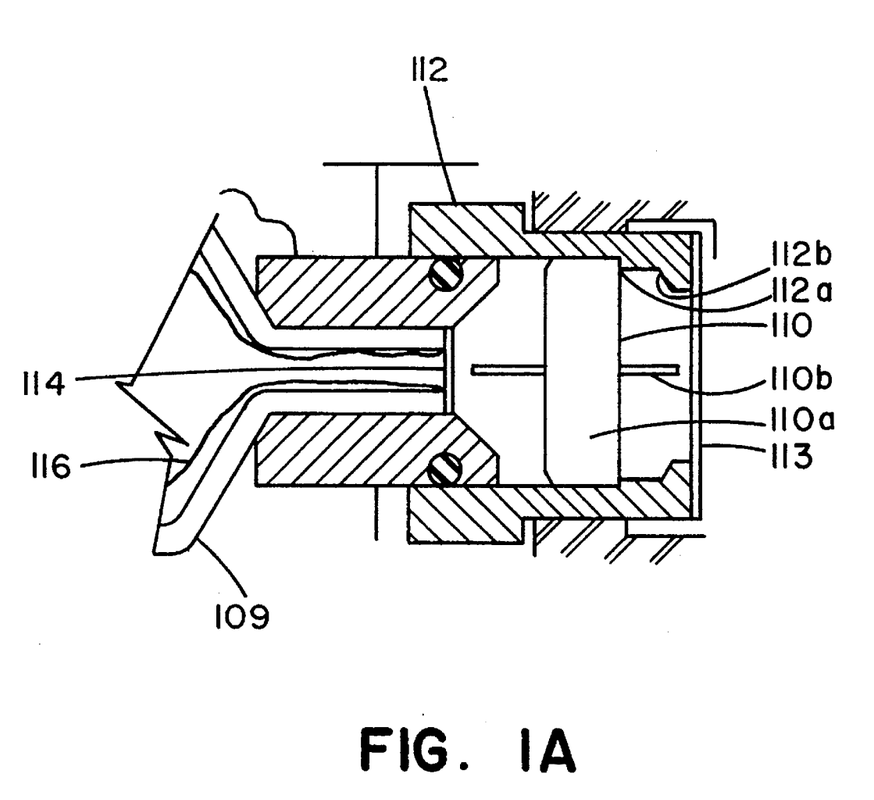
FIG. 1A is an exploded view of the knife blade assembly and knife blade collar with timing step depicted in FIG. 1.

The respective function of and of each of the aforementioned components and how they interact to accomplish the objectives of the invention as recited hereinbefore, will now be set forth in detail with further reference to FIG. 1, along with reference to FIG. 2. FIG. 1A may also be referred to for an exploded view of knife blade assembly 110 and the knife blade collar with timing step, 112, depicted in and described with reference to FIG. 1.

It is assumed, for the sake of illustration only, that a self curing bone cement formed as a polymeric reaction product when a powdered polymer component is mixed with a liquid monomer component, is being prepared for delivery during an operation, such as an operation to set an artificial joint.

It is also assumed that the components shown in FIG. 1 have been assembled as shown and include a sterile dry powdered polymer component stored in a sterile evacuated powder chamber 102, and a sterile liquid monomer stored in sterile monomer chamber 109. Monomer chamber 109 could, for example, be fabricated using molded materials, such as polyethylene. Powder/vacuum (mixing) chamber 102 may, for example, be comprised of injection-molded polyethylene and, in accordance with an illustrative embodiment of the invention, may be suitably evacuated to approximately 10" of pressure.

Chamber 102 is shown in FIG. 1 having one membrane at the dispensing end of device 100 (seal 117), and another membrane at the plunger (seal 113).

A second chamber, monomer chamber 109 shown in FIG. 1 to include flexible bladder 116, may be filled with monomer and may be stored under normal atmospheric pressure.

Techniques for introducing these components into chambers such as chambers 102 and 109, and insuring that the components are sterile, are well known by those skilled in the art. For example, powder/vacuum chamber 102 may be sterilized using gamma sterilization, and monomer chamber 109 can first be sterilized and then be aseptically filled by means of progressive filtration. Such techniques will not be further discussed herein since they do not constitute a part of the invention per se.

What is new, according to one aspect of the invention, is the process for preparing and delivering self curing bone cement formed by combining a powdered polymer component and a liquid monomer component, comprising the steps of: (a) storing the powdered polymer component in an evacuated mixing chamber; (b) storing the liquid monomer component in a separate pressurized component chamber; and (c) controlling the introduction of the liquid monomer component into the mixing chamber to substantially wet the powdered polymer component stored therein. These steps, along with others that insure that a durable cement product is readily prepared and delivered in an operative setting, will now be described in detail (along with suitable apparatus for performing these steps), with reference to FIG. 1.

To start the preparation and delivery sequence the user exerts force on (for example, pushes forward on) monomer chamber 109 depicted in FIG. 1.

Monomer chamber 109 will traverse forward and will push membrane mounting blocks 111 and membrane seal 114 against hollow needle knife blade assembly 110, causing membrane seal 114, which seals monomer chamber 109, is punctured by knife blade tube 110b shown in FIG. 1.

It should be noted that according to a preferred embodiment of the invention, the aforementioned mounting blocks 111 may, for example, be fabricated using molded materials, such as polyethylene. Additionally, according to a preferred embodiment of the invention, all seals described herein may be fabricated by, for example, utilizing a colaminate or single layer film.

It should be further noted that, according to a preferred embodiment of the invention, knife blade assembly 110 includes a knife blade collar 110a and a hollow "syringe like" knife blade tube, 110b. A first piercing edge on the proximal end of knife blade tube 110b functions to rupture seal 114 when mounting blocks 111, shown carrying seal 114, are pushed forward into tube 110b in the manner described hereinabove.

Collar 110a may, for example, be fabricated using a molded material such as polyethylene. Knife blade tube 110b may, for example, be metallic, having sharp notched ends designed to rupture and retain portions of the seals the ends come in contact with.

According to the description of the invention being set forth with reference to FIG. 1, Knife blade assembly 110 continues to move forward as continued force is applied to the rear exposed portion of monomer chamber 109 by the user.

According to a preferred embodiment of the invention (though not required to practice all embodiments of the invention), there is a split second delay, caused by the knife blade collar with timing step 112 with its timing step ridge 112a projecting into the lumen of knife blade assembly 110. After the delay, the edge of hollow needle knife blade assembly 110 closest to powder/vacuum chamber 102, punctures the membrane 113 which isolates the vacuum from the monomer.

According to a preferred embodiment of the invention, the timing step function may be realized by creating a resilient ridge on knife blade collar with timing step 112, with the ridge projecting into the lumen of knife blade assembly 110 (in particular, into the path of knife blade collar 110a), so that it keeps knife blade assembly 110 from traversing forward until sufficient pressure is applied to the collar. A portion of one such ridge, ridge 112a, is shown in FIG. 1. Ridge 112a is designed to come in contact with the side of knife blade collar 110a facing chamber 102.

Alternatively, the invention contemplates the use of a resilient knife blade collar which give way when forced against a rigid timing step ridge formed in the knife blade collar timing step, thereby allowing the knife blade collar to move forward at the appropriate time.

The purpose of ridge 112a is to prevent the knife blade from penetrating seal 113 before monomer seal 114 is broken. To insure a uniform mix and control the effects of the vacuum, timing is extremely important. In preferred embodiments of the invention, the discharge sequence is intended to be controlled by the aforementioned timing step or means which perform the equivalent sequenced discharge function.

According to a preferred embodiment of the invention, a further ridge is fabricated on the knife blade collar with timing step, exemplified by the knife blade assembly retainer ridge 112b shown in FIG. 1. The purpose of ridge 112b is to prevent knife blade collar 110a from interfering with the operation of the monomer component diffusion process.

It should be noted that the aforementioned knife blade collar with timing step may also serve as fixture blocks when assembling device 100.

Returning to the description of the invention from the point where seal 113 is broken, the vacuum pulls the monomer from the bladder 116 and as the monomer is evacuated from the bladder its volume is displaced with air via vent 116 shown in FIG. 1 as part of monomer chamber 109 (vent 116 is illustratively shown in the rear exposed portion of monomer chamber 109).

A description of how the monomer is evacuated from bladder 116 (or any other suitable monomer component storage device), into what literally becomes the mixing chamber (chamber 102) once both components are present therein, in a manner which is controlled to insure that the powder stored in chamber 102 is substantially wet, will now be set forth in conjunction with a description of the remaining elements of device 100 depicted in FIG. 1. It will become apparent to those skilled in the art how the objectives of the invention are achieved once the construction of device 100 is fully explained and understood. Accordingly, reference should again be made to FIG. 1 where the remaining elements of device 100 are depicted.

According to the illustrative embodiment of the invention depicted in FIG. 1, chamber 102 has what has been referred to hereinbefore as wire mesh screen 103, circumferentially running along inside the wall of the chamber, forming a "tubular" shaped screen. Furthermore, FIG. 1 depicts, running circumferentially along the inside the wall of wire mesh screen 103, what has been referred to as monomer circumferential diffuser with slitted plastic tube 104 (sometimes referred to hereinafter as "slit screen" 104).

For reasons to be explained hereinafter, slit screen 104 is preferably a polyethylene tube, which is itself "slitted" with approximately 0.25"-long slits running in a diagonal pattern across the entire area of the tube.

Wire mesh screen 103 and slit screen 104 (sometimes referred to herein as liquid component diffusion means) may be held in place within chamber 102 by the compressive force exerted by plunger head 106 against the interior wall of chamber 102, in which case the screens must have openings which allow the liquid monomer component to flow from thru the screens to those monomer distribution channels located (according to a preferred embodiment of the invention) in the wall of chamber 102 as may be seen with reference to FIG. 2 (showing exemplary monomer distribution channel 299 in chamber wall 202).

The purpose of the "double screen" (wire mesh screen 103 combined with slit screen 104) is to allow the monomer to first travel down the inside walls of chamber 102 (in, for example, monomer distribution channel 299 illustrated in FIG. 2), before being "dispersed through" wire mesh screen 103; while at the same time preventing the powder from clogging wire mesh screen 103 while the product is being transported, stored, etc.

The slits in tube 104 are preferably narrow enough so as to prevent the powder from penetrating through to wire mesh screen 103, yet when the vacuum seal is broken, the slits are flexible enough to allow the liquid monomer to rush through into the powder packed in chamber 102.

In one embodiment of the invention slit screen 104 is made of TEFLON(™). This material (or coating) will facilitate a smooth travel for the monomer chamber 109/plunger head 106 combination down the wall of chamber 102.

In addition to dispersing the liquid monomer to the periphery of chamber 102, according to the preferred embodiment of the invention, the liquid monomer is also delivered to the "core" of chamber 102. The concept, according to this one aspect of the invention, is to wet the powder from both outside and inside of the powder mass to enhance the wetting process.

To facilitate delivering liquid to the core of the powder mass center stem 105 (shown as part of the illustrative plunger head 106 assembly depicted in FIG. 1) is utilized.

The depicted plunger head 106 assembly also optionally incorporate stirring rod assembly 108 which can be used to stir (further mix) the two cement components once they are united.

Center stem 105 may be fabricated utilizing a narrow Teflon tube, approximately 0.25" in diameter, attached to plunger head 106. When fabricated in this manner, center stem 105 is a tube that is flattened and slitted similarly to slitted screen 104, described hereinbefore.

When monomer chamber 109 is pushed toward powder/vacuum chamber 102 and the vacuum is broken (as described hereinbefore), the liquid monomer rushes into chamber 102 and is diverted in two directions with (1) some of the monomer rushing down center stem 105 and out the slits in center stem 105 into the center of the packed powder; (2) while the remainder of the monomer will hit one of the walls of plunger head 106 and run radially out toward the inside wall of chamber 102 (through, for example monomer distribution channel 199 shown in FIG. 1), into the monomer distribution channels located in the wall of chamber 102

(like channel 299 shown in FIG. 2), down through wire mesh screen 103 running around the entire inside wall of chamber 102. From there the liquid penetrates through the slits of the large Teflon tube (slit screen 104), and rushes into the powder itself from the periphery of the powder pack.

In order to then mechanically mix the two cement components together, the aforementioned stirring rod assembly 108 may be incorporated into the plunger head 106 assembly. The stirring rod assembly, according to one embodiment of the invention, is comprised of a "U"-shaped 0.125" diameter rod with a collapsible wire mesh spanning the "U". When the user turns the monomer chamber "handle", this motion is translated to the stirring rod assembly, 108, and the assembly moves around to physically mix the two cement components.

As indicated hereinbefore, FIG. 2 depicts an exemplary stirring rod assembly 108 of the type shown attached to the plunger head in FIG. 1, along with exemplary liquid component diffusion means (wire mesh 103 and slit screen 104 of FIG. 1) which are both, according to a preferred embodiment of the invention, installed in the vacuum packed powder chamber.

In particular, FIG. 2 illustrates chamber 102 from FIG. 1, as chamber 202; where chamber 202 includes the exemplary monomer distribution channels referred to hereinbefore (those channels located in the wall of chamber 202 an exemplified by channel 299); membrane seal 217 (corresponding to seal 117 of FIG. 1); screens 203 and 204, corresponding respectively to screens 103 and 104 shown in FIG. 1); stirring rod assembly 208 (corresponding to stirring rod assembly 108 of FIG. 1), shown in combination with slitted center stem 205 (corresponding to center stem 105 of FIG. 1). Stirring rod assembly 208 is shown to include the "U" shaped tube and collapsible wire mesh (mixing filaments) referred to hereinabove, shown respectively in FIG. 2 as rod 208a and filaments 208b.

FIG. 2 also depicts stirring rod assembly 108 and center stem 205 attached to plunger head 206 which illustrates, although having a different geometry from the plunger head shown in FIG. 1 (plunger head 106 which is conically shaped), one manner in which the center stem, optional stirring rod assembly and the plunger head are meant to cooperate.

According to a one embodiment of the invention, at any time before, during or after the mixing procedure described hereinbefore (using the stirring rod assembly) is completed, the entire assembly depicted in FIG. 1 may be agitated (such as by manually shaking cartridge up and down), to ensure a more thorough mixing of the two components.

For most bone cement applications the user should wait 60–180 seconds before taking the steps described hereinafter for compressing the mixture to complete the mixing process and beginning a mixture dispensing phase in which the cement is delivered, as needed, in the operative setting. It should be noted that the end user can control the viscosity of the bone cement by allowing more or less time before initiating the compressing and dispensing operation referred to hereinabove.

Making further reference to FIG. 2 it should be noted that what has been referred to hereinbefore as primary vacuum seal 101 (shown as seal 201 in FIG. 2), is also illustrated. This seal may be ruptured via knife blade 115 when, for example, the user manually exerts force on monomer chamber 109, or when the compression phase of preparing the component mixture begins.

According to the illustrative embodiment of the invention depicted in FIG. 1, primary membrane seal 101 is positioned proximal to plunger 106, in-between monomer component chamber 109 (with knife blade 115 extending toward seal 101 therefrom), and plunger head 106. Alternatively, primary membrane seal 101 may be positioned distal to the plunger.

The purpose of primary membrane seal 101, which may, for example, be realized by a co-extruded or laminated film on the outside surface of plunger head 106, is to prevent plunger head 106 from being drawn into evacuated chamber 102 and also prevent loss of vacuum from evacuated chamber 102. Accordingly, it is preferred that this seal be broken just prior to the commencement of the mixture compression phase to be described hereinafter.

When the entire assembly 100 is loaded into a caulking-style gun (not shown) and the compression phase is begun, the monomer chamber is pushed forward—down the inside walls of the large Teflon tube of chamber 102, and after a brief travel starts to push on the back of the plunger head 106.

An example of a commercially available dispensing gun suitable for use in conjunction with device 100 depicted in FIG. 1 is the Howmedica Enhanced Bone Cement Gun, Model 6205-1-500.

The compression of the mixture serves as a vehicle for insuring a good, homogeneous mixture of the powder and monomer liquid before the cement is dispensed. For example, air trapped between the particles of stored powder and subsequently introduced into the mixture may be reduced through the compression that takes place as plunger head 106 is forced toward membrane seal 117 by the gun pressing on the rear exposed portion of monomer chamber 109.

Eventually, the force applied by the gun will cause membrane seal 117 (located at the distal end of mixing chamber 102) to be ruptured by the pressure of the plunger head 106 compressing the mixture. When this occurs, passageway is opened through which the prepared cement may flow from chamber 102.

For dispensing the polymerized cement mixture, the user continues to trigger the gun, forcing the mixture out through passageway 145 at a rate desirable to the user.

It should be noted that during the compression phase, both monomer chamber 109 and plunger head 106 will move down into chamber 102 together (corresponding to components 209, 206 and 202 respectively, shown in FIG. 2), and the aforementioned stirring rod 208a shown in FIG. 2 will pass through the back of plunger head 106 and monomer chamber 109; while the stirring assembly wire mesh (filaments 208b) simply collapse.

As a result, the polymerized cement compound will be forced out the front of assembly 100 with no interference from plunger head 106. Center stem 105, because it is "flattened", will simply move forward down the center of dispensing nozzle, and the cement will flow out around it.

Alternatively, the tip of center stem 105 may be "pointed" in form, so that the point will "cut" through dispensing membrane (seal 117) to allow the cement to flow out (instead of depending on sufficient pressure popping seal 117 at the end of the compression phase).

Further reference should be made to FIG. 1 which depicts O-ring plunger seal 107. O-ring plunger seal 107, which may be realized by use of a rubber O-ring seal, serves (in a preferred embodiment of the invention) to seal the vacuum in chamber 102 while the apparatus depicted in FIG. 1 is being stored; and keeps the mix contained in chamber 102 when device 100 depicted in FIG. 1 is in use.

To complete the description of the invention, still further reference should be made to FIG. 1 to note that plunger head 106 functions to support most of the components of the depicted device 100. It should be understood that plunger head 106 is designed in combination with the components used in any given device fabricated in accordance with the teachings set forth herein, to, for example, support and orient preselected diffusion means to enable the components being mixing to interact in accordance with the teachings of the invention.

According to the embodiment of the invention depicted in FIG. 1, plunger head 106 also includes a knife edge, shown as scraper blade 118, which functions to scrape the cement mix from the walls of chamber 102 during the cement dispensing process. Scraper blade 118 also serves to prevent highly viscous mixtures from working past the plunger during the compression phase of the mixing and dispensing processes.

Still further, with reference to FIG. 1, it should be noted that plunger head 106 is preferably designed to have the depicted conical shape when used in conjunction with a powder vacuum (mixing) chamber having a conical shaped distal end, such as chamber 102 depicted in FIG. 1. This design match enables the maximum amount of cement to be forced through passageway 145 in the manner described hereinabove. A suitable material for fabricating plunger head 106 is molded polyethylene.

The plunger head used in device 100 depicted in FIG. 1 (plunger head 106) is in and of itself believed to be novel and includes, as shown and described hereinabove, (a) means for controlling the introduction of a liquid component, stored in a pressurized chamber, to a multiplicity of different locations within an evacuated mixing chamber to substantially wet a powdered component stored therein, combined with (b) means for uniformly mixing the powdered component and the liquid component within the mixing chamber to thereby saturate the powdered component with the liquid component.

Finally, it should be noted (and those skilled in the art will readily appreciate), that an improved cement product is formed by the processes described herein. Accordingly, any products of the aforementioned processes (including noncementitious products) are meant to be included within the scope of the present invention.

What has been described in detail hereinabove are methods and apparatus meeting all of the aforestated objectives. As previously indicated, those skilled in the art will recognize that the foregoing description has been presented for the sake of illustration and description only. It is not intended to be exhaustive or to limit the invention to the precise form disclosed, and obviously many modifications and variations are possible in light of the above teaching.

For example, the methods and apparatus described herein were presented in the context of preparing a bone cement from a powdered polymer and liquid monomer component. However, those skilled in the art will readily appreciate that such methods and apparatus are well suited for mixing other powdered and liquid components, in application that are unrelated to the preparation of bone cement, using mixing system, plunger head design, etc., taught herein.

A further example systems contemplated by the invention would include those having a plurality of "exits" from the monomer chamber per se, as opposed to the single "exit" (through seal 114 of FIG. 1, once opened)) described hereinabove. In other words, totally separate passageways could have been used to feed a plurality of monomer distribution channels leading to different portions of the powder pack to try and achieve the substantial wetting objective set forth hereinabove in a predefined and controlled manner.

The embodiments and examples set forth herein were presented in order to best explain the principles of the instant invention and its practical application to thereby enable others skilled in the art to best utilize the instant invention in various embodiments and with various modifications as are suited to the particular use contemplated.

It is, therefore, to be understood that the claims appended hereto are intended to cover all such modifications and variations which fall within the true scope and spirit of the invention.

What is claimed is:

1. A method for preparing and delivering self curing bone cement mixture formed by combining a mass of powdered polymer component and a liquid monomer component, comprising the steps of:
   (a) storing said powdered polymer component pass in an evacuated mixing chamber;
   (b) storing said liquid monomer component in a separate pressurized component chamber; and
   (c) controlling the introduction of said liquid monomer component into said mixing chamber, including the step of wetting said powdered polymer component from outside and from within the stored powdered polymer component mass to thereby substantially wet the powdered polymer component mass stored in said mixing chamber.

2. A method as set forth in claim 1 wherein said step of controlling further comprises the step of delivering said liquid monomer in parallel to a multiplicity of different locations within said mixing chamber, including at least one location within the powdered polymer component mass stored in said mixing chamber.

3. A method as set forth in claim 1 wherein said step of controlling further comprises the step of utilizing a plurality of monomer distribution channels terminating in said mixing chamber to deliver said liquid monomer component thereto.

4. A method as set forth in claim 3 wherein said plurality of monomer distribution channels insure the distribution of said liquid monomer component to at least the center and periphery of said evacuated mixing chamber.

5. A method as set forth in claim 3 further comprising the step of utilizing one way monomer distribution channels to thereby allow the liquid monomer component to flow only towards and into said mixing chamber.

6. A method as set forth in claim 1 wherein said step of controlling further comprises the steps of:
   (a) opening said separate pressurized chamber; and
   (b) placing the liquid monomer component of said separate pressurized chamber in fluid communication with the powdered polymer component mass of said mixing chamber at a multiplicity of different locations therein.

7. A method as set forth in claim 6 wherein said step of placing further comprises the step of utilizing a plurality of monomer distribution channels, each including liquid component diffusion means terminating in said mixing chamber, to deliver said liquid monomer component to said mixing chamber.

8. A method as set forth in claim 7 wherein said step of opening further comprises the step of staging the release of said liquid monomer component into said mixing chamber.

9. A method as set forth in claim 8 wherein said step of staging further comprises the step of utilizing the combination of timing step means, seal piercing means and said liquid component diffusion means to stage the release of said liquid monomer component into said mixing chamber in a timed sequence.

10. A method as set forth in claim 9 wherein said combination is operative to first break a seal on said separate pressurized component chamber and then break a seal on said evacuated mixing chamber to thereby enable said liquid monomer component to be drawn from said separate pressurized component chamber, through said plurality of monomer distribution channels, into said evacuated mixing chamber via said liquid component diffusion means.

11. A method as set forth in claim 10 further comprising the step of preventing component and mixture backflow.

12. A method as set forth in claim 1 further comprising the step of stirring the liquid monomer component and powdered polymer component mass together after the liquid monomer component has been introduced into said mixing chamber.

13. A method as set forth in claim 1 further comprising the step of shaking the contents of said mixing chamber after the liquid monomer component has been introduced thereto.

14. A method as set forth in claim 1 further comprising the steps of:
    (a) stirring the liquid monomer component and powdered polymer component mass together after the liquid monomer component has been introduced into said mixing chamber; and
    (b) shaking the contents of said mixing chamber after the liquid monomer component has been introduced thereto.

15. A method as set forth in claim 14 further comprising the step of pressurizing the cement mixture in said mixing chamber to compress air out of said cement mixture.

16. A method as set forth in claim 15 further comprising the step of dispensing the compressed cement mixture from said mixing chamber.

17. A method as set forth in claim 16 wherein said step of dispensing said compressed cement mixture is performed by further pressurizing the mixture in said mixing chamber to break a seal between said mixing chamber and a dispensing nozzle leading out from said mixing chamber.

18. A method for saturating a predetermined mass of a powdered component with a predetermined volume of a liquid component as part of a component mixing process, comprising the steps of:
    (a) storing said powdered component mass in an evacuated mixing chamber;
    (b) storing said liquid component in a separate pressurized component chamber; and
    (c) controlling the introduction of said liquid component into said mixing chamber, including the step of wetting said powdered component mass from outside and from within the stored powdered component mass to thereby substantially wet the powdered component mass stored in said mixing chamber.

19. A method for mixing a powdered component mass with a liquid component comprising the steps of:
    (a) evacuating a first container containing a powdered component mass;
    (b) providing a second container containing a liquid component;
    (c) connecting said first and second containers, after the evacuation of said first container, allowing liquid component to be drawn into said first container; and
    (d) introducing said liquid component into said first container in a manner which substantially wets the powdered component mass stored therein by wetting said powdered component mass from outside and from within the stored powdered component mass.

20. A plunger head, for use as part of a system for mixing a powdered component, stored in an evacuated mixing chamber into which the distal end of said plunger head extends, with a liquid component, stored in a pressurized chamber attached to the proximate end of said plunger head, comprising:
    (a) means for controlling the introduction of said liquid component stored in said pressurized chamber to a multiplicity of different locations within said evacuated mixing chamber to substantially wet the powdered component stored therein; and
    (b) means for uniformly mixing said powdered component and said liquid component within said mixing chamber thereby saturating said powdered component with said liquid component.

21. Apparatus as set forth in claim 20 wherein said means for controlling the introduction of said liquid component into said mixing chamber utilizes the vacuum in said evacuated mixing chamber to draw said liquid component therein.

22. Apparatus as set forth in claim 21 wherein said means for controlling further comprises:
    (a) means for opening said separate pressurized chamber; and
    (b) means for placing the liquid component of said separate pressurized chamber in fluid communication with the powdered component of said mixing chamber at a multiplicity of different locations therein.

23. Apparatus as set forth in claim 22 wherein said means for placing further comprises a plurality of liquid component distribution channels, each including liquid component diffusion means terminating in said mixing chamber, to deliver said liquid component to said mixing chamber.

24. Apparatus as set forth in claim 23 wherein said means for opening further comprises means for staging the release of said liquid component into said mixing chamber.

25. Apparatus as set forth in claim 24 herein said means for staging further comprises:
    (a) timing step means for staging the release of said liquid component into said mixing chamber in a timed sequence; and
    (b) seal piercing means cooperating with said timing step means.

26. Apparatus as set forth in claim 23 wherein said means for controlling is operative to first break a seal on said separate pressurized component chamber and then break a seal on said evacuated mixing chamber to thereby enable said liquid component to be drawn from said separate pressurized component chamber, through said plurality of distribution channels, into said evacuated mixing chamber via said liquid component diffusion means.

27. Apparatus as set forth in claim 26 wherein said liquid component diffusion means further comprises:
    (a) means for enabling said liquid component to enter said mixing chamber; and
    (b) means for preventing said powdered component from inhibiting the flow of said liquid monomer component into said mixing chamber.

28. Apparatus as set forth in claim 27 wherein said liquid component diffusion means further comprises a double screen which includes an outside wire mesh screen portion and an interior slit screen portion, the combination of which allows said liquid component to enter said mixing chamber while preventing said powdered component from inhibiting the flow of said liquid component into said mixing chamber.

29. Apparatus as set forth in claim 28 wherein said powdered component is a polymer used as a component in a bone cement mix.

30. Apparatus as set forth in claim 28 wherein said liquid component is a monomer used as a component in a bone cement mix.

31. Apparatus as set forth in claim 26 wherein said liquid component diffusion means is operative to prevent component and mixture backflow.

32. Apparatus as set forth in claim 31 wherein said liquid component diffusion means further comprises the combination of a wire mesh screen and a slitted plastic tube.

33. Apparatus as set forth in claim 32 wherein said tube is coated with TEFLON™ brand non-stick coating.

34. Apparatus as set forth in claim 20 wherein said means for controlling further comprises a center stem through which said liquid component may be introduced into said evacuated mixing chamber.

35. Apparatus as set forth in claim 34 wherein said means for uniformly mixing further comprises a stirring assembly, combined with said center stem, for stirring said liquid and said powdered component after said liquid component has been introduced into said mixing chamber.

36. Apparatus as set forth in claim 35 wherein said stirring assembly further comprises a "U" shaped rod have a collapsible wire mesh spanning said rod.

37. A mixing device for mixing a powdered and a liquid component comprising:
    (a) a first evacuated container containing a powdered component mass;
    (b) a second container containing a liquid component;
    (c) means for connecting said first and second containers, after the evacuation of said first container, allowing said liquid component to be drawn into said first container, and
    (d) means for introducing said liquid component into said first container in a manner which substantially wets the powdered component mass stored therein by wetting said powdered component mass from outside and from within the stored powdered component mass.

38. The mixing device of claim 37 further including means for dispensing said liquid and powdered components which have been mixed.

39. The mixing device of claim 38 wherein said first container is cylindrical in shape and has a first end with a dispensing nozzle and said means for dispensing is a plunger slidably mounted within a second open end of said cylindrical first container.

40. The mixing device as set forth in claim 38 wherein said first container has a breakable seal formed thereon for retaining the evacuated condition thereof.

41. The mixing device as set forth in claim 38 wherein said second container is operative to allow atmospheric pressure to act on the liquid component thereof to force said liquid component into said first container upon the connection of said second container to said evacuated first container.

42. Apparatus for preparing and delivering a self curing bone cement mixture formed as a polymeric reaction product when a powdered polymer component is mixed with a liquid monomer component, comprising:
    (a) an evacuated first component chamber for storing said powdered polymer component mass;
    (b) a second component chamber for storing said liquid monomer component;
    (c) means for controlling the introduction of said liquid monomer component, stored in said second component chamber, to a multiplicity of different locations within said first component chamber, including locations outside and within the stored powdered polymer component mass, to thereby substantially wet the powdered polymer component mass stored in said mixing chamber;
    (d) means for uniformly mixing said powdered polymer component mass and said liquid monomer component within said first component chamber thereby saturating said powdered polymer component mass with said liquid monomer component.

43. Apparatus as set forth in claim 42 wherein said means for controlling the introduction of said liquid monomer component into said first component chamber utilizes the vacuum in said first component chamber to draw said liquid monomer component therein.

44. Apparatus as set forth in claim 43 wherein said means for controlling further comprises:
    (a) means for opening said second component chamber; and
    (b) means for placing the liquid monomer component of said second component chamber in fluid communication with the powdered polymer component mass of said first component chamber at a multiplicity of different locations therein.

45. Apparatus as set forth in claim 44 wherein said means for placing further comprises a plurality of liquid component distribution channels, each including liquid component diffusion means terminating in said first component chamber, to deliver said liquid monomer component to said first component chamber.

46. Apparatus as set forth in claim 45 wherein said means for opening further comprises means for staging the release of said liquid monomer component into said first component chamber.

47. Apparatus as set forth in claim 46 wherein said means for staging further comprises:
    (a) timing step means for staging the release of said liquid monomer component into said first component chamber in a timed sequence; and
    (b) seal piercing means cooperating with said timing step means.

48. Apparatus as set forth in claim 45 wherein said means for controlling is operative to first break a seal on said second component chamber and then break a seal on said first component chamber to thereby enable said liquid monomer component to be drawn from said second component chamber, through said plurality of distribution channels, into said evacuated first component chamber via said liquid component diffusion means.

49. Apparatus as set forth in claim 48 wherein said liquid component diffusion means further comprises:
    (a) means for enabling said liquid monomer component to enter said first component chamber; and
    (b) means for preventing said powdered polymer component mass from inhibiting the flow of said liquid monomer component into said first component chamber.

50. Apparatus as set forth in claim 49 wherein said liquid component diffusion means further comprises a double screen which includes an outside wire mesh screen portion and an interior slit screen portion, the combination of which allows said liquid monomer component to enter said first component chamber while preventing said powdered polymer component mass from inhibiting the flow of said liquid monomer component into said first component chamber.

51. Apparatus as set forth in claim 48 wherein said liquid component diffusion means is operative to prevent component and mixture backflow.

52. Apparatus as set forth in claim 51 wherein said liquid component diffusion means further comprises the combination of a wire mesh screen and a slitted plastic tube.

53. Apparatus as set forth in claim 52 wherein said tube is coated with TEFLON™ brand non-stick coating.

54. Apparatus as set forth in claim 42 wherein said means for controlling further comprises a center stem through which said liquid monomer component may be introduced into said evacuated first component chamber.

55. Apparatus as set forth in claim 54 wherein said means for uniformly mixing further comprises a stirring assembly, combined with said center stein, for stirring said liquid monomer and said powdered polymer component mass after said liquid monomer component has been introduced into said first component chamber.

56. Apparatus as set forth in claim 55 wherein said stirring assembly further comprises a "U" shaped rod have a collapsible wire mesh spanning said rod.

57. Apparatus as set forth in claim 54 further comprising means for pressurizing the cement mixture in said first component chamber to compress air out of said cement mixture.

58. Apparatus as set forth in claim 57 further comprising means for dispensing the compressed cement mixture from said first component chamber.

59. Apparatus as set forth in claim 57 wherein said means for dispensing comprises a plunger head that includes said means for controlling and said means for uniformly mixing.

60. Apparatus for preparing a homogeneous self-curing two component powder/liquid bone cement mixture using a vacuum packed powdered polymer chamber containing a powder polymer mass into which liquid monomer is introduced, comprising:

(a) a pressurized chamber for storing said liquid monomer;

(b) a vacuum packed powder chamber for storing said powdered polymer mass; and (c) means for controlling the introduction of said liquid monomer into said vacuum packed powder chamber to locations outside and within the stored powdered polymer mass, to thereby substantially wet the powdered polymer mass stored therein.

61. Apparatus as set forth on claim 60 wherein said means for controlling further comprises means for delivering said liquid monomer in parallel to a multiplicity of different locations within said powder chamber.

62. Apparatus as set forth in claim 60 wherein said means for controlling further comprises means for delivering said liquid monomer to said powder chamber utilizing a plurality of monomer distribution channels terminating in said powder chamber.

63. Apparatus as set forth in claim 62 wherein said plurality of monomer distribution channels insure the distribution of said liquid monomer to at least the center and periphery of the powder chamber.

64. Apparatus as set forth in claim 62 wherein said plurality of monomer distribution channels are one way channels allowing only the liquid monomer to flow towards and into said powder chamber.

65. Apparatus as set forth in claim 60 wherein said means for controlling further comprises:

(a) means for opening said powder chamber; and (b) means for placing the liquid monomer of said pressurized chamber in fluid communication with the powdered polymer mass of said powder chamber at a multiplicity of different locations therein.

66. Apparatus as set forth in claim 65 wherein said means for placing utilizes a plurality of monomer distribution channels, each including liquid component diffusion means terminating in said powder chamber, to deliver said liquid monomer to said powder chamber.

67. Apparatus as set forth in claim 66 wherein said means for opening further comprises means for staging the release of said liquid monomer into said powder chamber.

68. Apparatus as set forth in claim 67 wherein said means for staging further comprises the combination of timing step means, seal piercing means and said liquid component diffusion means to stage the release of said liquid monomer into said powder chamber in a timed sequence.

69. Apparatus as set forth in claim 68 wherein said combination is operative to first break a seal on said pressurized chamber and then break a seal on the evacuated powder chamber to thereby enable said liquid monomer to be drawn from said pressurized chamber, through said plurality of monomer distribution channels, into said powder chamber via said liquid component diffusion means.

70. Apparatus as set forth in claim 69 wherein said liquid component diffusion means is operative to prevent component and mixture backflow.

71. Apparatus as set forth in claim 60 further comprising means for stirring the liquid monomer and powdered polymer mass together after the liquid monomer has been introduced into said powder chamber.

72. Apparatus as set forth in claim 60 further comprising:

a) means for stirring the liquid monomer and powdered polymer mass together after the liquid monomer has been introduced into said powder chamber; and (b) means for pressurizing the cement mixture to compress air out of said mixture.

73. Apparatus for as set forth in claim 72 further comprising means for dispensing the compressed cement mixture.

\* \* \* \* \*